United States Patent [19]

Zimmerly

[11] Patent Number: 5,275,201
[45] Date of Patent: Jan. 4, 1994

[54] MANIFOLD VALVE ASSEMBLY WITH REMOVABLE VALVE SEAT

[75] Inventor: Robert D. Zimmerly, Kenosha, Wis.

[73] Assignee: Tri-Clover, Inc., Kenosha, Wis.

[21] Appl. No.: 918,238

[22] Filed: Jul. 23, 1992

[51] Int. Cl.$^5$ .............................................. F16K 11/10
[52] U.S. Cl. .................................. 137/454.6; 137/597; 137/625.5
[58] Field of Search ................... 137/454.6, 597, 625.5

[56] References Cited

U.S. PATENT DOCUMENTS

| | | | |
|---|---|---|---|
| 916,403 | 3/1909 | Adamson | 137/625.5 |
| 1,579,503 | 4/1926 | Bloch | 137/625.5 |
| 1,937,246 | 11/1933 | Reedy | 137/625.5 X |
| 2,348,238 | 5/1944 | Beeke et al. | 137/625.5 X |
| 3,744,376 | 7/1973 | Carpenter | 137/597 X |
| 4,250,920 | 2/1981 | Traylor | 137/625.5 X |
| 4,757,834 | 7/1988 | Mieth | 137/15 |
| 5,141,012 | 8/1992 | Gavrilla | 137/454.6 X |

OTHER PUBLICATIONS

Tri-Flow 761 Valve Series, Publication No. BTN761, Oct., 1992, p. 6.
Triclover Automated Flow Control Catalogue No. AFC-92, Mar., 1992, p. 4.
Tuchenhagen Varivent Brochure, no date.
Alfa-Laval Koltek Mix Proof Valve Brochure, Apr. 15, 1991.
Sudmo Double Seat Valve Brochure, Jul., 1991.
Alfa-Laval Flow Equipment Sanitary Mix Proof Valve Instructions and Parts List, 1982.

Primary Examiner—Stephen M. Hepperle
Attorney, Agent, or Firm—Ryan, Kees & Hohenfeldt

[57] ABSTRACT

A flow control manifold assembly, constructed of a number of manifold valve assemblies. Each manifold valve assembly is formed of first and second valve bodies, each body having at least one inlet port and a plurality of outlet ports. The two valve bodies are connected together in fluid communication with each other. Associated with each valve body is an actuator assembly, which includes a valve actuator and an actuator rod attached to and projecting outward from the actuator, and actuatable by the actuator. In at least one of the valve bodies, a bonnet is affixed to the actuator, and projects into the respective one of the valve bodies. A valve stem, carrying at least one valve plug, is attached to the projecting end of the actuator rod, positioning the valve plug on the opposite side of the bonnet from the actuator. The bonnet includes a valve seat for engagement with the valve plug when the valve plug is actuated to a predetermined position by the actuator. One embodiment provides a third valve body, also in fluid communication with the first valve body, so that flow from one source to two destinations can be controlled by a single valve assembly. Thus the invention replaces a single, expensive, multiple-actuator valve with a pair of inexpensive single-actuator valves which together are less expensive than the single valve they replace, while still preventing the mixing of different types of fluids.

19 Claims, 5 Drawing Sheets

MANIFOLD VALVE ASSEMBLY WITH REMOVABLE VALVE SEAT

BACKGROUND OF THE INVENTION

This invention relates to valves for controlling the flow of fluids, and particularly to block-and-bleed valves assembled together to form manifolds for controlling the flow of fluids from multiple sources to multiple delivery destinations. Certain concerns unique to the sanitary industry are discussed.

It is common in the food packaging industry to have a need to connect a number of sources of a fluid, such as different types of milk, to a number of different filler machines to fill containers, such as gallons, half-gallons, quarts and so on. To date these connections have been accomplished in the form of a manifold, including a number of lines from the source tanks crossing a number of lines leading to the filler machines, with the valves being provided to permit or prevent flow of fluid from any selected one or more of the source tanks to any chosen one or more of the filler machines. This arrangement creates a need for an extremely large number of valves, however. For instance, a single manifold connecting ten source tanks to ten filler machines, would use over a hundred valves to accomplish the control which is necessary and desired.

In the past, it has been conventional to use specially designed valves to control these manifolds, called block-and-bleed valves, sometimes called leak detector valves, with one such valve installed at each manifold intersection. Block-and-bleed valves are particularly applicable to the sanitary industry, because they permit control of flow of different types of fluids through the same valve with double protection against intermixing of those fluids. That is, it may be desirable to have chocolate milk flowing through one part of the valve and white milk through another part, or pasteurized milk through one part and raw milk through another part, or clean-in-place solution through one part and milk or another food fluid through another part. Clearly it is critical that these fluids not be permitted to mix, and regulations require that even failure of a single seat or valve plug not permit that mixing.

The type of valve used in the past functioned generally satisfactorily in most instances. Being a single valve, however, it was required to be extremely complex and expensive, including multiple, coaxial, independently operable actuators and valve plugs. Under certain circumstances these valves were subject to substantial leakage and product waste, and when they did fail in this manner, while preventing mix of different fluids, their maintenance was difficult and expensive.

This invention relates to improvements to the apparatus described above, and to solutions to some of the problems raised or not solved thereby.

SUMMARY OF THE INVENTION

The present invention includes a manifold valve assembly, formed of first and second valve bodies, each body having at least one inlet port and a plurality of outlet ports. The two valve bodies are connected together in fluid communication with each other. Associated with each valve body is an actuator assembly, which includes a valve actuator and an actuator rod attached to and projecting outward from the actuator, and actuatable by the actuator. In at least one of the valve bodies a bonnet is affixed to the actuator, insertable into the respective valve body. At least one valve stem is attached to the projecting end of the actuator rod, with plugs on the opposite side of the bonnet from the actuator. The bonnet includes a valve seat for engagement with one of the valve plugs when that valve plug is actuated to a predetermined position by the actuator. Thus the invention replaces a single, expensive, multiple-actuator block-and-bleed valve with several simple, inexpensive single-actuator valves which together are substantially less expensive than the single valve they replace, while still preventing the mixing of different types of fluids, even on failure of one valve seat or valve plug.

Other objects and advantages of the invention will become apparent hereinafter.

DESCRIPTION OF THE DRAWING

FIG. 6 is an exploded side elevational view, partially in cross-section, of the valve shown in FIG. 4.

FIG. 7 is a side elevational view of a bonnet constructed according to an alternative embodiment of the invention.

DESCRIPTION OF THE PREFERRED EMBODIMENT

Figure 1:
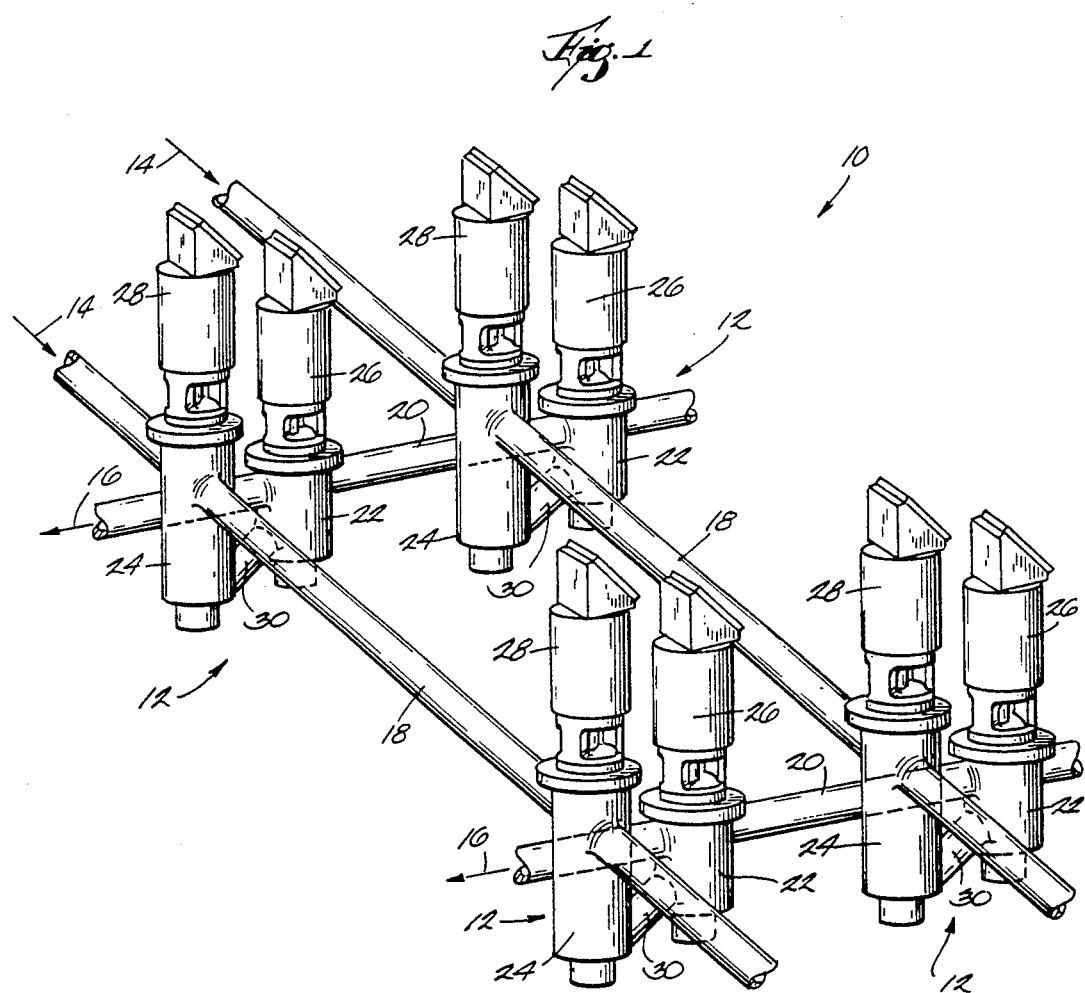
FIG. 1 is a perspective view of a manifold assembly employing manifold valve assemblies constructed according to one embodiment of the invention.

Referring now to FIG. 1, there is shown a manifold assembly 10, employing a number of manifold valve assemblies 12 constructed according to one embodiment of the invention. As there shown, the manifold assembly 10 is connected to and receives supply from a number of sources 14, such as tanks of fluid. The manifold assembly 10 is also connected to and supplies the fluid to a number of destinations 16, such as filler machines for filling containers with one or more of the fluids from the fluid supply tanks. The purpose of the manifold assembly 10 is to control and selectively permit the flow of fluid from one or more predetermined sources 14 to a predetermined destination 16. The manifold assembly includes one supply tube 18 for each fluid supply source 14, and one delivery tube 20 for destination 16. While the manifold assembly 10 shown in FIG. 1 includes only two supplies 14 and two destinations 16, it will be understood that the invention may be equally well applied to any number of supplies and destinations.

As can be seen from FIG. 1, this manifold assembly results in a crossed pattern of supply tubes 18 and delivery tubes 20. The supply tubes 18 and delivery tubes 20 do not actually intersect, but rather are positioned parallel in sets, in parallel planes, with either one set or the other being in the upper plane, the opposite set being in the lower plane. According to the embodiment of the invention shown in the drawing figures, the delivery tubes 20 are positioned in a plane beneath the plane of the supply tubes 18, but it could just as easily be the other way around. One manifold valve assembly 12 is provided at each crossing point of a supply tube 18 with a delivery tube 20.

Figure 2:
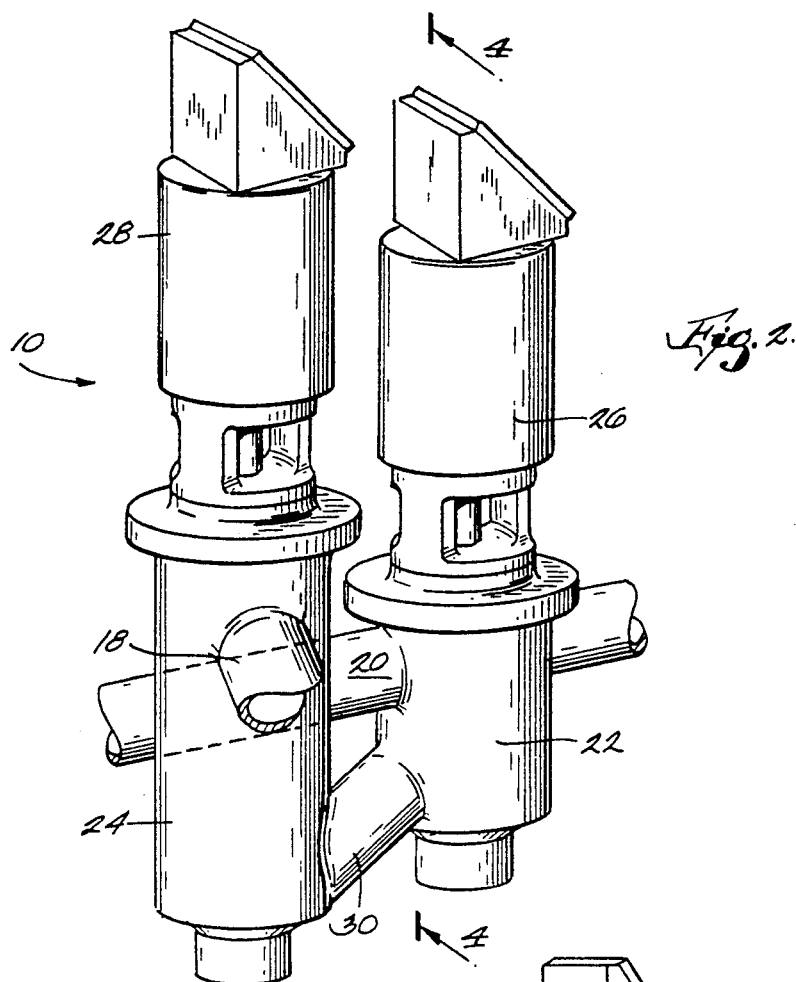
FIG. 2 is a perspective view of a manifold valve assembly such as those shown in FIG. 1, constructed according to one embodiment of the invention.
Figure 3:
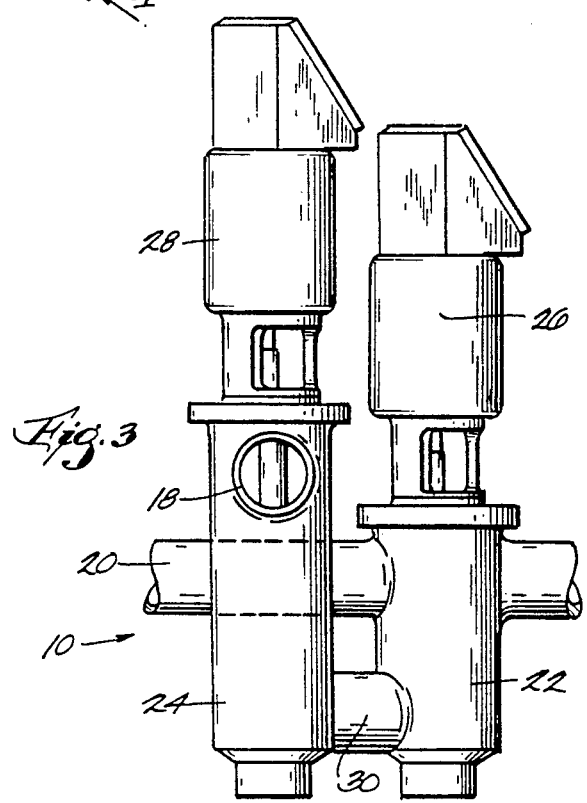
FIG. 3 is a side view of the manifold valve assembly shown in FIG. 2.

As shown best in FIGS. 2 and 3, each manifold valve assembly 12 includes in effect two separate valve bodies, a delivery valve body 22 and a supply valve body 24. Each of these valve bodies 22, 24 is supplied with its own actuator assembly 26, 28 respectively. As shown in FIGS. 2 and 3, these valve bodies 22, 24 are connected by a short crossover tube 30. As can best be seen in FIG. 3, this crossover tube 30 is positioned at the very bottom of each valve body, and oriented substantially horizontally between the two. Also as shown in FIG. 3, because the supply tubes 18 are positioned in a plane higher than that of the delivery tubes 20, the supply valve body 24 is longer than the delivery valve body 22, by approximately the diameter of the delivery tube and the vertical spacing between the delivery tube and the supply tube.

Figure 4:
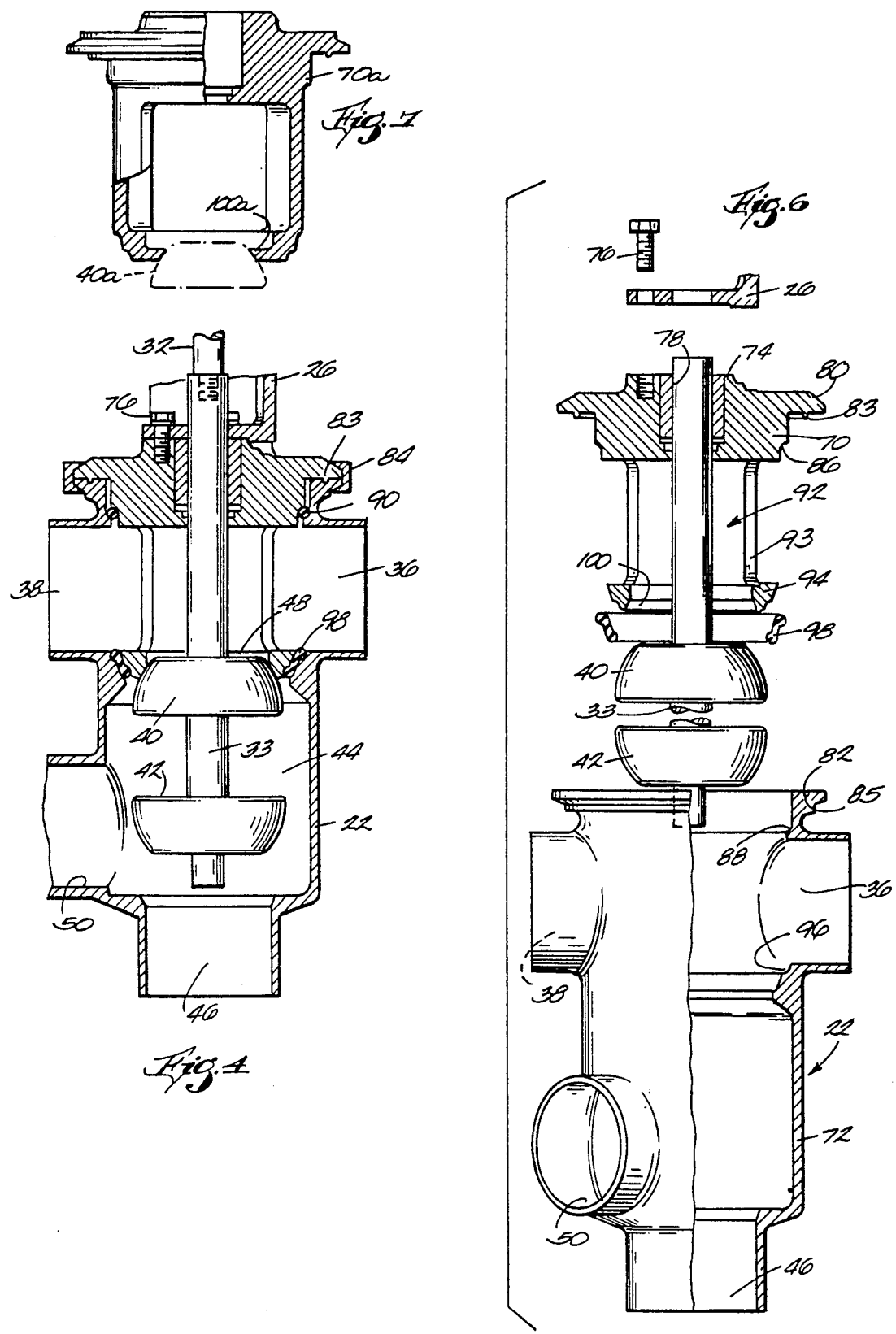
FIG. 4 is a cross-sectional view of one of the valves making up the manifold valve assembly shown in FIGS. 2 and 3, taken along line 4—4 of FIG. 2.
Figure 5:
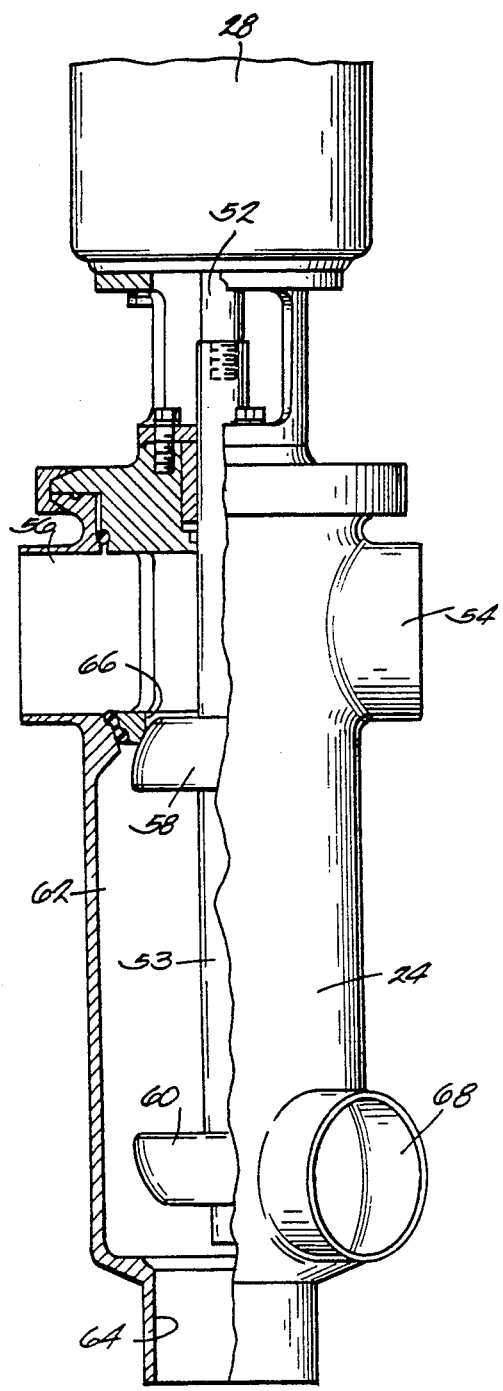
FIG. 5 is a view, partially in cross-section, of the other of the valves making up the manifold valve assembly shown in FIGS. 2 and 3.

The interior detail of each valve body can been seen by reference to FIGS. 4 and 5. FIG. 4 shows the detail of the delivery valve body 22, while FIG. 5 shows the detail of the supply valve body 24. Reference will first be had to the detail of the delivery valve body 22, and this detail will later be related to the detail of the supply valve body 24.

As indicated above, referring particularly to FIG. 4, delivery valve body 22 includes its own actuator 26, having an actuator rod 32, actuatable between two positions. Valve body 22 has, at its top, a pass-through section including an inlet 36 substantially aligned with an outlet 38. Relating FIG. 4 with FIG. 1, the inlet 36 and outlet 38 of the delivery valve body 22 connect to and in effect form part of one of the delivery tubes 20, permitting free flow of fluid to fluid destinations 16 from upstream destination valves at all times.

As is not uncommon in sanitary valves, a valve stem 33 is attached to actuator rod 32 by any suitable, removable means, such as by a threaded attachment. Two valve plugs, an upper plug 40 and a lower plug 42, are attached to or integrally formed with the valve stem 33, both plugs positioned within a valve cavity 44 of the delivery valve body 22 after assembly of the valve stem to the actuator rod 32. Lower plug 42 is positioned on valve stem 33 to be capable of closing a drain port 46 at the bottom of valve cavity 44, while upper plug 40 is positioned thereon to be capable of closing a cavity outlet port 48 at the top of the valve cavity. The actuator 26 basically has two positions, one where drain port 46 is open and cavity outlet port 48 is closed, and the other where drain port 46 is closed and cavity outlet port 48 is open. Valve cavity 44 also has a cavity inlet port 50, which communicates with crossover tube 30, shown in FIGS. 1 and 2.

As also indicated above, referring now mainly to FIG. 5, supply valve body 24 has its own actuator 28. As with delivery valve body 22, again actuator 28 has an actuator rod 52, actuatable between two positions. Supply valve body 24 has, at its top, a pass-through section including an inlet 54 substantially aligned with an outlet 56. Relating FIG. 5 with FIG. 1, the inlet 54 and outlet 56 of the supply valve body 24 connect to and in effect form part of one of the supply tubes 20, permitting free flow of fluid from fluid sources 14 to downstream supply valves at all times.

As with delivery valve body 22, actuator rod 52 has affixed thereto a valve stem 53, by any suitable removable means, such as by threading. Two valve plugs, an upper plug 58 and a lower plug 60, are affixed to or integrally formed with the valve stem 53. Once the valve stem 53 is assembled to the actuator rod, both plugs 58, 60 are positioned within a valve cavity 62 of the supply valve body 24. Lower plug 60 is positioned on valve stem 53 to be capable of closing a drain port 64 at the bottom of valve cavity 62, while upper plug 58 is positioned to be capable of closing a cavity inlet port 66 at the top of the valve cavity. As was the case with delivery actuator 26, supply actuator 28 has two positions, one where drain port 64 is open and cavity inlet port 66 is closed, and the other where drain port 64 is closed and cavity inlet port 66 is open. Valve cavity 62 also has an cavity outlet port 68, which communicates via crossover tube 30 with cavity inlet port 50 of delivery valve body 22, shown in FIGS. 1, 2 and 4.

Thus when cavity inlet port 66 is closed, the fluid in inlet 54 is not permitted to enter cavity 62, and continues out outlet 56, possibly to the next manifold valve assembly 12. When actuator 28 moves actuator rod 52 to its other position, taking valve stem 53 and valve plugs 58, 60 with it, cavity inlet port 66 is opened and drain port 64 is closed, permitting flow of fluid into the cavity 62 via the cavity inlet port 66 and permitting flow of the fluid out of the cavity via cavity outlet port 68. Control of the two actuators 26 and 28 is coordinated so that when cavity outlet port 48 of delivery valve body 22 is open, cavity inlet port 66 of supply valve body 24 is also open. Fluid then flows from supply tube 18 into supply valve cavity 62, through crossover tube 30, into delivery valve cavity 44, and finally into delivery tube 20.

Since as indicated above the length of the body of the valve bodies 22, 24 is different, correspondingly the length of the delivery valve stem 33 must differ from the length of the supply valve stem 53 by the same amount. That is, because the supply valve body 24 is longer than the delivery valve body 22, the delivery valve stem 53 will also be longer than the supply valve stem 33 by about the same amount. As can be seem by comparing FIG. 4 to FIG. 5, that difference is applied to the distance between respective pairs of valve plugs, so that the distance between delivery valve plugs 40 and 42 is smaller than the distance between supply valve plugs 58 and 60 by substantially the same amount.

As indicated above, the actuators 26, 28 are coordinated to normally work together. Otherwise the supply valve cavity inlet port 66 could be open while delivery valve cavity outlet port 48 is closed, causing supply fluid to drain continuously out delivery valve drain port 64. Accordingly, any malfunction of any part of the manifold valve assembly 12 must be quickly restored to proper function to minimize waste. However, once the number of manifold valve assemblies 12 is assembled into the manifold assembly 10, usually by welding, there would be no practical means to easily remove and/or replace a single valve body.

Therefore the invention calls for structure permitting easy removal of the actuator and valve stem from any one of the valves at any time. This feature of the invention can best be set forth by reference to FIG. 6, using a delivery valve body 22 as an example, although it clearly applies equally to the supply valve body 24 in this embodiment. As shown there, the body 22 is formed by the assembly of a valve bonnet 70 into a valve body proper 72, the latter having substantially all the ports 36, 38, 46, 50 referred to above. The only port formed specifically by the bonnet 70 is the cavity outlet port 48, in the following manner.

The valve stem 33 is inserted upward through an opening 78 in the bonnet 70 and attached to actuator rod 32. The actuator 26, with the valve stem 33 attached to its actuator rod 32, is then affixed to a flat top surface 74 of the bonnet by any suitable removable means, such as threaded fasteners 76. The bonnet 70 has a flange 80 which flares outward from the central opening, to fit onto a mating flange surface 82 of the body proper 72. Upon assembly the two flanges are clamped together by a suitable clamp 84 (FIG. 4). An annular ridge 83 is provided in the facing surface of the bonnet flange 80, which engages a matching annular channel 85 formed in the facing surface of the mating flange surface 82, to aid in alignment and assembly. Beyond the flange 80, the bonnet 70 includes a shoulder 86 which, together with a facing shoulder structure 88 in the body proper 72, permits spacing for sealing means, such as an O-ring 90 (FIG. 4). After the shoulder 86, the bonnet 70 has a cage portion 92, with large openings or gaps alternating with separated bars 93. The cage portion 92 is about the same in length as the inlet port 36 and outlet port 38 are in width. The bonnet 70 then terminates in a ring portion 94, which contacts a corresponding ledge 96 in the body proper 72, via another sealing means 98 (FIGS. 4 and 6). In its preferred form, sealing means 98 can best be described as either a gasket having enlarged side edges or a pair of O-rings integrally connected by a web. The ring portion 94 has an inner beveled area 100 at its distal end which constitutes a valve seat into which plug 40 is sized to tightly fit.

Once valve stem 33 is inserted through opening 78 in bonnet 70 and attached to actuator rod 32, the entire assemblage is then inserted into the body proper 72 and clamped therein. Just as easily, if the actuator 26 requires service, or if the valve plugs 40, 42 need replacing or other service, the clamp 84 is opened and the actuator and bonnet 70 removed.

Thus the structure of the present invention replaces a single, expensive, multiple-actuator valve with a pair of simple, inexpensive single-actuator valves which together are less expensive than the single valve they replace, while still preventing the mixing of different types of fluids, even on failure of one valve seat or valve plug. It is not uncommon for the single valve of the prior art to be three times as expensive as one of the simple valves provided by the present invention. Accordingly, even though the present invention requires in effect two valves where the prior art used one, the cost of the structure of the present invention is still less than the prior art by a third or more.

It is not unusual for the delivery tubes 16 to be smaller in size than the supply tubes 14, such as 2 inch delivery tubes being used with 3 inch supply tubes. In order to satisfy sanitary requirements, it is necessary that the total drain opening area of the manifold valve assembly 12 is at least as large as the smaller of the supply tubes 14 or the delivery tubes 16. In most prior art valves, this requirement adds to the expense of the valve, requiring a large single opening. In the structure provided by the present invention, however, in effect two drain ports are provided, one drain port 46 in the delivery valve body 22 and one drain port 64 in the supply valve body 24. It is the sum of the areas of these two drain ports that must at least equal the area of the smaller of the supply tube 14 or delivery tube 16. Each separate drain port 46, 64 can, then, be substantially smaller than either the supply tube 14 or the delivery tube 16. This has the further advantage of permitting the relative reduction of the size of the valve cavities 44, 62, reducing waste of product. Waste is reduced because each time the valve actuators 26, 28 switch from open to closed, the entire volume of fluid in both valve cavities 44, 62 is drained out the respective drain port. If the volume of these cavities is reduced, the volume of fluid wasted in switching is also reduced. Even further, as shown in FIG. 7, a bonnet 70a may be provided with a smaller seat 100a, the diameter of the seat being reduced to substantially the size of the delivery tube 20. This bonnet 70a permits reduction of the size of the plug 40a, further reducing waste.

FIGS. 8 through 11 show manifold valve structure to accomplish the same objects, but from a slightly different approach. In the embodiments shown in those figures, only one specialized valve body is used, with the remaining control provided by simple shut-off valves.

Figure 8:
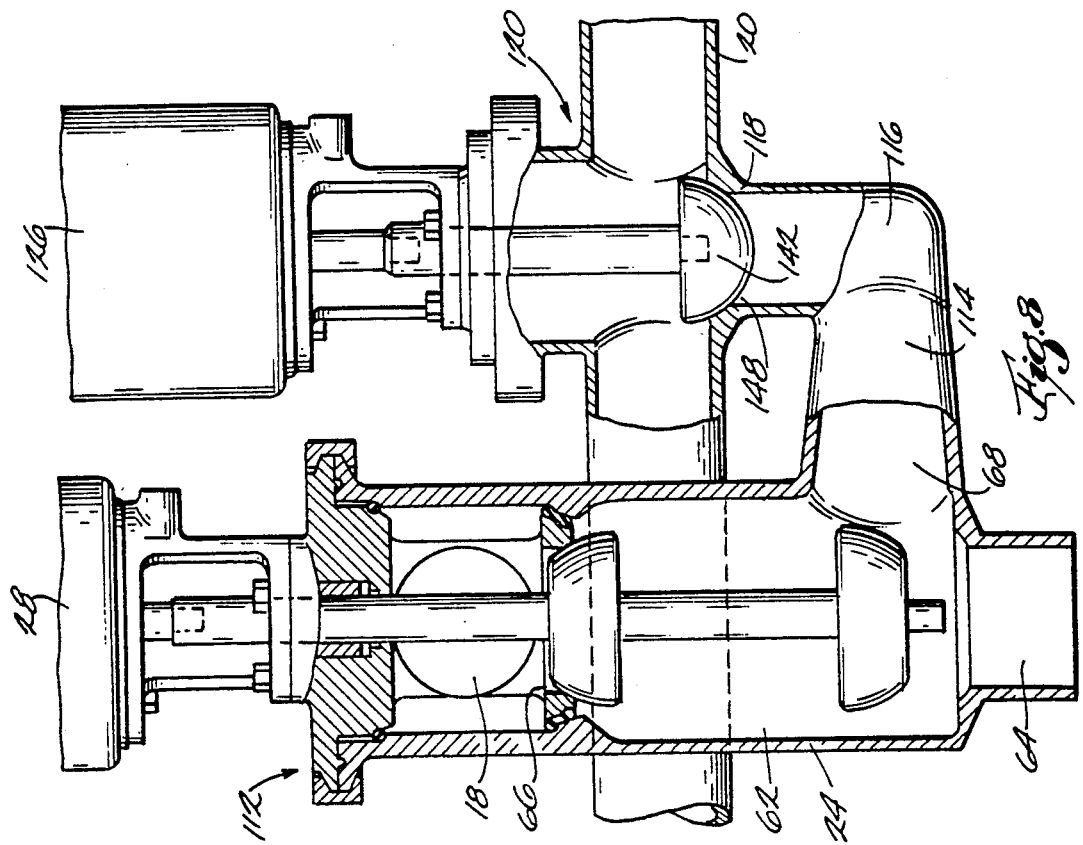
FIG. 8 is a side elevational view, partially cut away, of a manifold valve assembly constructed according to an alternative embodiment of the invention.

Referring particularly to FIG. 8, there is shown a manifold valve assembly 112 having a supply valve body 24 exactly as described above with reference to FIGS. 1 through 3 and particularly FIG. 5. In this embodiment, however, supply valve cavity outlet port 68 is connected to a short length of tubing 114 and an elbow 116, in turn connected to the inlet 118 of a conventional shut-off valve 120. The type of shut-off valve 120 selected is the type with a T-body, as the shut-off valve still needs to be connected into the delivery tube 20 and permit pass-through of the fluid in the delivery tube Hence the flow within manifold valve assembly 112 begins when actuator 28 opens cavity inlet port 66 and closes drain port 64. At the same time shut-off valve actuator 126 withdraws plug 142 from shut-off valve outlet port 148. The fluid flowing into cavity 62 then continues and flows through tubing 114 and elbow 116, and thereby through shut-off valve 120 and into delivery tube 20.

Figure 9:
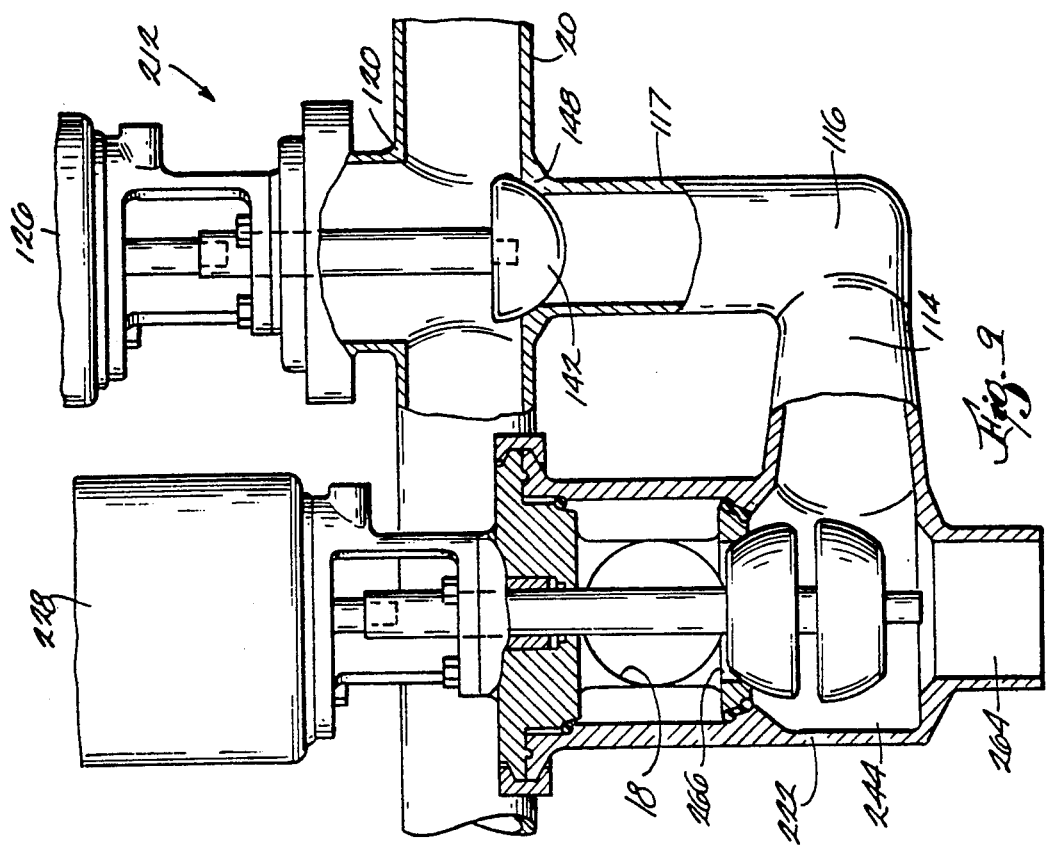
FIG. 9 is a side elevational view, partially cut away, of a manifold valve assembly constructed according to another alternative embodiment of the invention.

It will be noted that the embodiment shown in FIG. 8 is applied to the situation where the plane of the supply tubes 18 is above the plane of the delivery tubes 20. As indicated earlier, either set of tubes may be in the upper plane. If the plane of the supply tubes 18 is below that of the delivery tubes 20, the manifold valve assembly 212 shown in FIG. 9 is used. Manifold valve assembly 212 includes a supply valve body 222 substantially identical to delivery valve body 22 (FIGS. 1 through 4 and 6), including the fact that the valve cavity 244 is shorter than the valve cavity 62 of supply valve 24 (FIG. 8). The only difference is the way the valve body 222 is connected into the manifold 10, that is, in such a way that the flow within the valve body is reversed from that described in reference to delivery valve body 22. In particular, when actuator 228 opens cavity inlet port 266 and closes drain port 264, shut-off valve actuator 126 simultaneously withdraws plug 142 from shut-off valve outlet port 148. The fluid flowing into cavity 244 then continues and flows through tubing 114 and elbow 116, and also through an extension 117 which must be provided because shut-off valve 120 is higher in assembly 212 than in assembly 112 to align with the relatively higher delivery tube 20. The fluid is thereby passed through shut-off valve 120 and into delivery tube 20.

The embodiments shown in FIGS. 8 and 9 have a slight advantage over that shown in the earlier drawing figures in that since there is no second specialized valve body, the amount of fluid inside the manifold valve assembly 112 or 212 is less, reducing waste.

Figure 11:
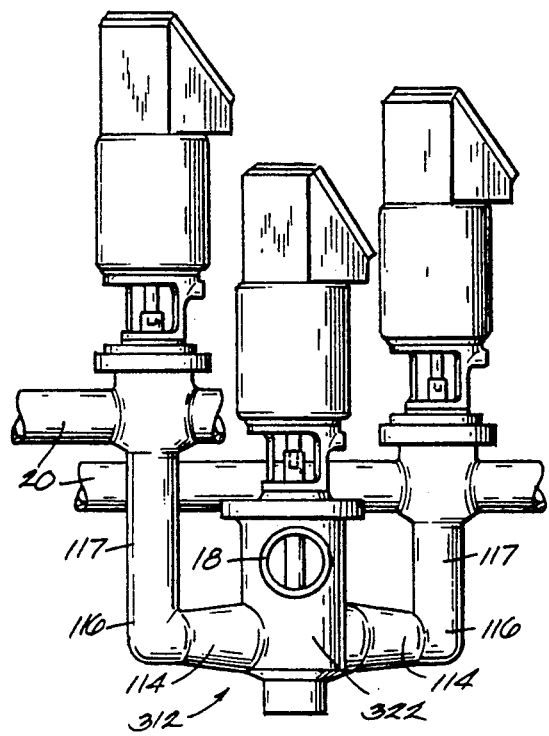
FIG. 11 is a side elevational view, partially in section, of a manifold valve assembly constructed according to the embodiment shown in FIG. 10.
Figure 10:
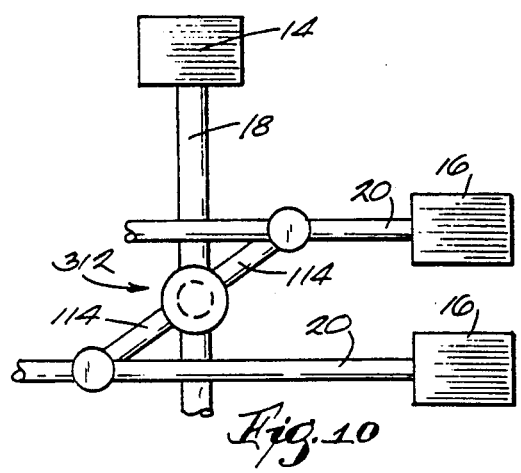
FIG. 10 is a schematic view of a manifold assembly employing manifold valve assemblies constructed according to yet another alternative embodiment of the invention.

Taking the embodiments shown in FIGS. 8 and 9 one step further is the embodiment shown in FIGS. 10 and 11. The manifold valve assembly 312 there shown includes three valves, two conventional shut-off valves 120 with T-bodies, with their inlets both connected, via respective extensions 117, elbows 116 and tubes 114, to separate outlets of specialized valve body 322. Valve body 322 is substantially the same as valve body 222, with the exception of the second outlet, for connection to the second shut-off valve. This arrangement permits, with the use of only one specialized valve body 322, the control of flow from a source 14 to two destinations 16, further reducing the total cost of the manifold without any loss of control and with reduced waste. Manifold valve assembly 312 replaces two of the previous, expensive valves, with a cost factor still less than one of those prior valves, while still preventing the mixing of different types of fluids running through the same valve assembly, even on failure of one valve seat or valve plug.

While the apparatus hereinbefore described is effectively adapted to fulfill the aforesaid objects, it is to be understood that the invention is not intended to be limited to the specific preferred embodiment of manifold valve assembly with removable valve seat set forth above. Rather, it is to be taken as including all reasonable equivalents within the scope of the following claims.

I claim:

1. A manifold valve assembly, for controlling flow between a first pipe connected to a source of fluids and a second pipe connected to a fluid delivery tube comprising:
   a first valve body, having at least one inlet port and a plurality of outlet ports said inlet port being connected to said first pipe, one of said outlet ports being connected to a drain and another one of said outlet ports being connected to a crossover conduit;
   a second valve body, also having at least one inlet port and at least one outlet port connected to said second pipe;
   said first and second valve bodies being connected in fluid communication with each other by said crossover conduit which connects an inlet port of said second valve body to an outlet port of said first valve body;
   an actuator assembly in said first valve body including:
   a valve actuator, an actuator rod attached to and actuatable by said actuator, one end of said rod projecting outward from said actuator,
   a bonnet affixed to said actuator, and insertable into said first valve body, and a valve stem attached to the projecting end of said actuator rod, having at least one valve plug positioned on the side of said bonnet opposite said actuator after assembly of said valve stem to said actuator rod for opening and closing said drain outlet port,
   said bonnet including a valve seat for engagement with said valve plug when said valve plug is actuated to a predetermined position by said actuator for opening and closing said inlet port.

2. A manifold valve assembly as recited in claim 1 wherein said valve bodies each include a valve cavity, and wherein said valve bodies are connected in fluid communication by means of said crossover tube connected between said valve cavity of said first valve body and said valve cavity of said second valve body.

3. A manifold valve assembly as recited in claim 1 wherein each of said valve bodies includes a pass-through area in fluid flow communication with either an inlet or an outlet, said pass through area not being controlled by said valve plug.

4. A manifold valve assembly as recited in claim 3 wherein said bonnet includes a cage portion positioned in said pass-through area, so as to continuously permit flow through the bonnet.

5. A manifold valve assembly as recited in claim 1 further comprising sealing means positioned between said bonnet and said valve body.

6. A manifold valve assembly as recited in claim 5 wherein said sealing means comprises a gasket having enlarged side edges.

7. A manifold valve assembly as recited in claim 5 wherein said sealing means comprises a pair of O-rings integrally connected by a web.

8. A manifold valve assembly as recited in claim 1 further comprising a second actuator assembly including:
   a second valve actuator,
   a second actuator rod attached to and actuatable by said second actuator, one end of said second rod projecting outward from said second actuator,
   a second bonnet affixed to said actuator, and insertable into the other of said valve bodies, and
   a second valve stem attached to the projecting end of said second actuator rod, having at least one valve plug positioned on the side of said second bonnet opposite said second actuator after assembly of said second valve stem to said second actuator rod,
   said second bonnet including a valve seat for engagement with said valve plug when said valve plug is actuated to a predetermined position by said second actuator.

9. A manifold valve assembly as recited in claim 1 further comprising a third valve body also in fluid communication with said first valve body, and having its own actuator.

10. A manifold assembly, for controlling flow between at least two sources of fluids and at least two fluid delivery tubes comprising:
    a plurality of manifold valve assemblies; means for connecting at least two of said manifold valve assemblies to respective ones of at least two supply sources;
    means for connecting at least two of said manifold valve assemblies to respective ones of at least two delivery outlets;
    each of said manifold valve assemblies including: a first valve body, having at least one inlet port and a plurality of outlet ports said inlet port being connected to a fluid source, one of said outlet ports being connected to a drain and another one of said outlet ports being connected to a crossover conduit; a second valve body, also having at least one inlet port and at least one outlet port connected to a fluid delivery tube;

said first and second valve bodies being connected in fluid communication with each other by said crossover conduit which connects an inlet port of said second valve body to an outlet port of said first valve body;

an actuator assembly in said first valve body including: a valve actuator, an actuator rod attached to and actuatable by said actuator, one end of said rod projecting outward from said actuator, a bonnet affixed to said actuator, and insertable into one of said valve bodies, and at least one valve plug attached to the projecting end of said actuator rod on the opposite side of said bonnet from said actuator for opening and closing said drain outlet port, said bonnet including a valve seat for engagement with said valve plug, when said valve plug is actuated to a predetermined position by said actuator for opening and closing said inlet port.

11. A manifold assembly as recited in claim 10 wherein each of said valve bodies includes a pass-through area in fluid flow communication with either an inlet or an outlet, said pass through area not being controlled by said valve plug, and wherein said first valve body includes a pass-through area for one of said supply sources.

12. A manifold assembly as recited in claim 11 wherein said second valve body includes a pass-through area for one of said delivery outlets.

13. A manifold assembly as recited in claim 11 or claim 12 wherein said bonnet includes a cage portion positioned in said pass-through area, so as to continuously permit flow through the bonnet.

14. A manifold assembly as recited in claim 10 further comprising sealing means positioned between said bonnet and said valve body.

15. A manifold assembly as recited in claim 14 wherein said sealing means comprises a gasket having enlarged side edges.

16. A manifold assembly as recited in claim 14 wherein said sealing means comprises a pair of O-rings integrally connected by a web.

17. A manifold assembly as recited in claim 10 wherein said valve bodies each include a valve cavity, and wherein said valve bodies are connected in fluid communication by means of a crossover tube connected between said valve cavity of said first valve body and said valve cavity of said second valve body.

18. A manifold assembly as recited in claim 10 further comprising a third valve body also in fluid communication with said first valve body, and having its own actuator.

19. A manifold assembly as recited in claim 18 wherein each of said three valve bodies includes a pass-through area not controlled by said valve plug, and wherein said first valve body includes a pass-through area for one of said supply sources, and second and third valve bodies each includes a pass-through area for a different one of said delivery outlets.

* * * * *